(12) United States Patent
Berkhof et al.

(10) Patent No.: US 11,998,669 B2
(45) Date of Patent: Jun. 4, 2024

(54) BREAST PUMP APPARATUS (71) Applicant: KONINKLIJKE PHILIPS N.V., Eindhoven (NL)

(72) Inventors: Rens Berkhof, Eindhoven (NL); Daan Anton Van Den Ende, Breda (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1386 days.

(21) Appl. No.: 16/468,923

(22) PCT Filed: Dec. 15, 2017

(86) PCT No.: PCT/EP2017/082955
§ 371 (c)(1),
(2) Date: Jun. 12, 2019

(87) PCT Pub. No.: WO2018/114637
PCT Pub. Date: Jun. 28, 2018

(65) Prior Publication Data
US 2019/0336661 A1    Nov. 7, 2019

(30) Foreign Application Priority Data
Dec. 19, 2016  (EP) .................................... 16205137

(51) Int. Cl.
*A61M 1/06* (2006.01)
*H10N 30/20* (2023.01)
*H10N 30/857* (2023.01)

(52) U.S. Cl.
CPC .............. *A61M 1/06* (2013.01); *A61M 1/066* (2014.02); *A61M 1/0697* (2021.05); *H10N 30/204* (2023.02); *H10N 30/857* (2023.02); *A61M 1/06935* (2021.05); *A61M 2205/0283* (2013.01);
(Continued)

(58) Field of Classification Search
CPC .............. A61M 1/06–0697; A61M 2205/0283
See application file for complete search history.

(56) References Cited

U.S. PATENT DOCUMENTS

| 4,799,922 A | 1/1989 | Beer |
| 5,571,084 A | 11/1996 | Palmer |
| 5,831,371 A | 11/1998 | Bishop |

(Continued)

FOREIGN PATENT DOCUMENTS

| CN | 1799436 A | 7/2006 |
| CN | 205339681 U | 6/2016 |

(Continued)

*Primary Examiner* — Courtney B Fredrickson (57) ABSTRACT

Based in the field of breastfeeding, a breast pump apparatus (100) for expressing breast milk is disclosed. The breast pump apparatus (100) comprises a container unit (110) for receiving expressed breast milk, and a pump unit (120) including a pump body (130) and a pumping device (140) for applying negative pressure to a pump volume defined by the pump body (130). The pump body (130) comprises an inlet portion (132) adapted to be received on a female breast and an outlet portion (134) adapted to channel expressed milk to the container unit (110). The pump body (130) comprises an actuator element (200, 300, 400) comprising an active material capable of deforming upon application of a control signal to it, wherein deformation of the actuator element modifies at least one of a shape and size of the pump volume.

20 Claims, 9 Drawing Sheets

(52) U.S. Cl.
CPC .............. *A61M 2205/106* (2013.01); *A61M 2205/3344* (2013.01)

(56) References Cited

U.S. PATENT DOCUMENTS

| | | | |
|---|---|---|---|
| 8,830,174 B1* | 9/2014 | Rodoper | G06F 3/0221 |
| | | | 345/169 |
| 10,213,535 B2 | 2/2019 | Tanaka | |
| 2006/0106334 A1 | 5/2006 | Jordan | |
| 2011/0190695 A1* | 8/2011 | Thilwind | A61M 1/064 |
| | | | 604/74 |
| 2012/0083731 A1 | 4/2012 | Gottenbos | |
| 2012/0116298 A1 | 5/2012 | Van Schijndel | |
| 2014/0276629 A1 | 9/2014 | Bauer | |
| 2015/0297442 A1 | 10/2015 | Bauer | |
| 2016/0058928 A1 | 3/2016 | Nowroozi | |
| 2016/0206794 A1 | 7/2016 | Makower | |
| 2016/0271305 A1 | 9/2016 | Kurihara | |
| 2016/0291603 A1 | 10/2016 | Chin | |
| 2017/0035951 A1* | 2/2017 | Tanaka | A61M 1/0693 |
| 2017/0136160 A1* | 5/2017 | Barral | A61M 1/0697 |

FOREIGN PATENT DOCUMENTS

| | | | | |
|---|---|---|---|---|
| EP | 0693788 A1 | 1/1996 | | |
| KR | 200440602 Y1 | 6/2008 | | |
| WO | WO-2004063090 A2 * | 7/2004 | ........... | B81B 3/0018 |
| WO | 2015183470 A2 | 12/2015 | | |
| WO | 2016024558 A1 | 2/2016 | | |
| WO | 2016033107 A1 | 3/2016 | | |

* cited by examiner

BREAST PUMP APPARATUS

This application is the U.S. National Phase application under 35 U.S.C. § 371 of International Application No. PCT/EP2017/082955, filed on Dec. 15, 2017 and International Application No. 16205137.9, filed Dec. 19, 2016. These applications are hereby incorporated by reference herein.

FIELD OF THE INVENTION

The present invention relates to the field of breastfeeding and in particular a breast pump apparatus. The present invention relates in particular to such breast pump apparatus having an adaptive pump body with a deformable actuator element comprising electroactive materials (EAM).

BACKGROUND OF THE INVENTION

Figure 1:
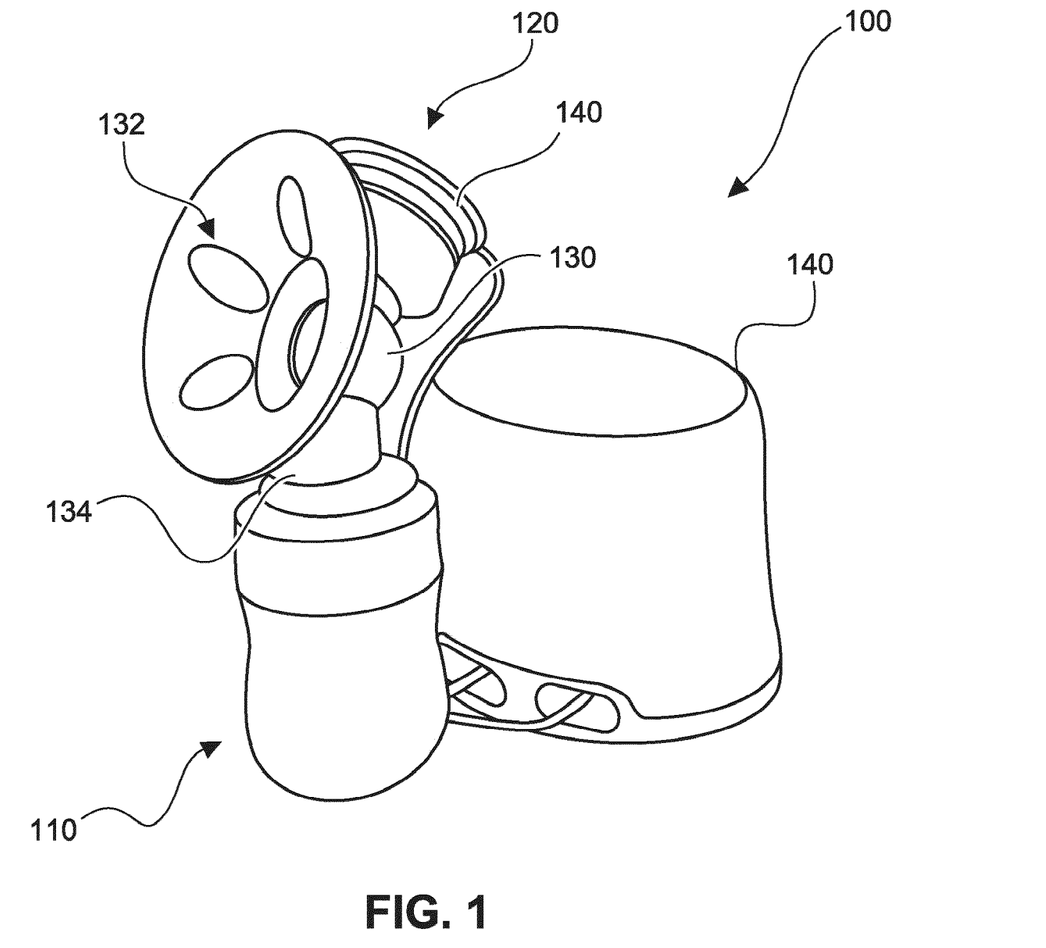
FIG. 1 shows schematically and exemplarily an embodiment of a breast pump apparatus according to the state of the art.

Breast pumps for extracting milk from breasts of lactating women are known. One example of a known breast pump is illustrated in FIG. 1. A breast pump apparatus 100 comprises a pump unit 120 including a pump body 130 and a pumping device 140. The pump body 130 defines a pump volume out of which pumping device 140 extracts air in order to apply a negative pressure to simulate the suckling of an infant while breastfeeding. In this example, pumping device 140 comprises an electrical pumping device which is, for the ease of handling, partly located separate from pump body 130.

In operation, an inlet portion 132 is received on a female breast and breast milk is extracted through the application of the negative pressure and channeled through an outlet portion 134 to a container unit 110. Usually, the container unit comprises a bottle which is removable from the breast pump in order to prepare the extracted breast milk for feeding the infant and/or for storage.

In the illustrated example, the inlet portion 132 comprises a massage cushion which is designed to feel soft and warm and imitates the baby's sucking action to provide milk flow. The massage cushions are available in different sizes to accommodate for different breast sizes.

However, a user's breasts may also change in size and firmness during the course of the breastfeeding time span, the inlet portion 132 can therefore not always fit seamlessly such that, despite being available in different sizes, it is not always possible to achieve a good vacuum and thus suction performance. The user needs to push the massage cushion or inlet portion 132 against the breast in order to achieve good vacuum, which can cause potential discomfort and irritation with the user.

Further, the suction performance is also affected by the user's nipple size. Large nipples will partly fill the pump body 130, while small nipples will fill the pump body 130 to a lesser extent, thus leading to a larger free volume within the pump body 130, which affects build-up of vacuum.

Finally, massaging and stimulation of the breast has a proven influence on the milk volume expressed by lactating women, which has to be done manually until now.

It has therefore been an object of the present invention to provide an improved breast pump apparatus, which overcomes at least some of the disadvantages and inconveniences known in the prior art.

SUMMARY OF THE INVENTION

In one aspect a breast pump apparatus for expressing breast milk is provided. The breast pump apparatus comprises a container unit for receiving expressed breast milk, and a pump unit including a pump body and a pumping device for applying negative pressure to a pump volume defined by the pump body. The pump body comprises an inlet portion adapted to be received on a female breast and an outlet portion adapted to channel expressed milk to the container unit. The pump body further comprises an actuator element comprising an active material capable of deforming upon application of a control signal to it and configured to have a bi-stable or multi-stable configuration, wherein deformation of the actuator element modifies at least one of a shape and size of the pump volume.

Since the pump body is capable of deforming and since the deformation of the actuator element modifies at least one of a shape and size of the pump volume, the pump volume and thus the pump body and the entire breast pump apparatus is adjustable to the particular user's needs. Expressed differently, the actuator element comprising electroactive material assists in obtaining optimal suction characteristics through adaptive elements influencing shape and/or size of the pump volume upon actuation. The control signal is applied to the actuator element by a control unit of the breast pump apparatus, for instance.

The pumping device can be an electrically or manually operated pumping device applying a negative pressure on the pump volume. For instance, in case of an electrical pumping device, the pumping device can comprise a motor unit and a diaphragm used for building-up and maintaining a negative pressure within the pump volume. Since different breast and nipple shapes and sizes account for a different shape and/or percentage of the pump volume being occupied by the female breast upon use, different negative pressure characteristics will be the result. This undesired effect can be account acted by modifying at least one of the shape and size of the pump volume by actuating the actuator element.

Preferentially, the inlet portion seals to the breast and closes the pump volume from the outside. In one embodiment, the inlet portion comprises a massage cushion which aims at providing a soft and warm feeding and imitates the baby's sucking action to improve milk flow.

The control signal can preferably be any type of control signal as long as it is suitable for causing an actuation of the actuator element. Thus, the control signal can be an optical control signal. In that case the electroactive material must also respond to application of optical signals with a deformation. The person skilled in the art will know where to find such materials in the art. In such case, the arrangement of the device can comprise units for guiding optical signals to a first part of the material. Such units can comprise mirrors, lenses optical fibers etc. However, the control signal can of course also be an electrical actuation signal.

The active material is a material that can deform or change its shape when a control signal is applied, i.e. the actuator element is driven. Driving can mean e.g. electrical driving (with voltage, field or current) or optical driving (with an optical signal of some frequency, color and/or intensity. Electro- or optoactive materials are materials that show mechanical deformation when electrically or optically driven with a suitable control signal. Certain classes of these materials also exhibit the converse effect, i.e. they can provide an electrical or optical signal when subjected to mechanical deformation, which will be described in further embodiments. The exact mechanism by which the above effects occur is dependent on the material of choice and in some cases also on the way of embedding them in a device. Because of the above effects, the application of such materials in actuators and/or sensors is advantageous in the breast pump apparatus according to the invention.

In an embodiment the actuator element comprises an electroactive material (EAM), in particular an electroactive polymer (EAP).

The group of EAPs is an emerging class of materials. They combine their favorable actuation-response properties with a number of advantageous engineering properties, therewith allowing use in new application areas. Thus, e.g. an EAP generally exhibits a relatively large deformation and force in a small volume or thin form factor, compared to common other mechanical actuators or actuators based on inorganic EAMs. EAPs also give noiseless operation, accurate electronic control, fast response, and the possibility of high resolution and cyclic actuation with a large range of possible actuation frequencies, such as 0-20 kHz. And all of these properties and advantages come with easy manufacturing into various shapes using well established methods allowing easy integration into a large variety of systems.

EAP materials can generally be divided in two classes with different properties, namely dielectric EAPs and ionic EAPs.

First, dielectric EAPs are materials in which actuation is caused by electrostatic forces between two electrodes which squeeze the polymer and actuators based thereon typically requires a large actuation voltage but low electrical power consumption. Dielectric EAPs require no power to keep the actuator at a given position. Examples are electrostrictive polymers and dielectric elastomers.

In contrast, in ionic EAPs actuation is caused by the displacement of ions inside the polymer. Only a low voltage is needed for actuation, but generally energy is needed to keep the actuator at a given position. Examples of ionic EAPs include conjugated/conductive polymers, ionic polymer-metal composites (IPMCs), and carbon nanotubes (CNTs). Other examples include ionic polymer gels.

Alternatively or additionally to EAPs, also other EAMs such as optoactive materials (OAM) can be employed. OAMs can comprise polymers having one or more double bonds which can undergo cis-trans isomerization upon irradiation. Such bonds can be C=C, N=C or N=N bonds. Such materials can included for example stilbenes.

In an embodiment the EAP comprises an ionic EAP.

Since the breast pump apparatus is intended to be used in contact with a female breast, the use of ionic EAPs is particularly preferred since it is inherently safe for skin contacting areas. For instance, the activation of ionic polymers requires only one to two volts and can thus be brought into contact with the skin without putting the user at risk.

In an embodiment the actuator element is further configured to operate as a pressure sensor. EAMs are known which exhibit an electrical or even optical signal when subjected to mechanical deformation, which can be advantageously employed to infer the pressure applied onto the actuator element itself. In this embodiment, since actuation and pressure sensing can both be realized using the same actuator element, the operation of the breast pump apparatus and particularly the deformation of the actuator element can be monitored such that the individual adaptation to a user can be further improved.

Preferably, in this embodiment the control signal comprises two control signals to be applied to the actuator element, wherein a first control signal is to control the deformation of the actuator element and a second control signal is employed in sensing by the device. The device is thus controlled using a control signal that is effectively composed of an actuation signal and a sensing signal. It is convenient to use the electroactive property of the actuator used for the sensing to also actuate the actuator. In this case the actuation signal is preferably an electrical actuation signal and the device and/or the electroactive structure can comprise one or more electrode arrangements for applying such actuation control signal. The actuator element, due to the electroactive material, responds to an electric field or force generated by such field. Hence, at least the sensing signal is an electrical signal so that mechanical resonance of the actuator can be determined from that electrical sensing signal.

The actuation signal and sensing signal, when both are electrical in this embodiment, can be provided separately to one or more electrode arrangements, but can also be superposed to from a combined control signal before providing the combined control signal to one or more electrode arrangements. Preferably, there is only one and the same electrode arrangement for providing the actuation and sensing signal to.

The actuator elements according to the embodiments of the invention make use of the following effect. When the sensing signal is applied at a frequency matching the mechanical resonance frequency, or one of its harmonics, of the EAM structure, a mechanical standing wave is established in the structure which in turn affects the electrical characteristics of the structure. In particular, the impedance of the structure is lower for a sensing signal (and thus for that part of control signal) matching the resonance frequency, due to the mechanical vibration being in-phase with the sensing signal. Conversely, the impedance of the material is higher for a sensing signal matching the anti-resonance frequency of the material (i.e. the $1^{st}$ harmonic of the resonance frequency), due to the mechanical vibration being out of phase with the sensing signal. It appears that at such frequencies sensing is extremely effective while it does not disturb longer term simultaneous actuation.

Any mechanical load, such as for example a pressure, applied to the electroactive structure may cause a damping in the structure, causing its resonance frequency (and the harmonics of the resonance frequency) to shift away from their ordinary un-damped values, thereby inducing a disparity between the high-frequency sensing signal and the frequency of mechanical vibration (or $1^{st}$ harmonic of this frequency, in the case of anti-resonance matching). All changes of characteristics of the resonant electroactive material structure caused by the change of the shift in resonance frequency can be advantageously used to detect a mechanical load with increased sensitivity. Thus, a shift in resonance frequency can be detected and/or determined. Detection and or determination of impedance can be done with advantage as will be elucidated herein below. The above holds for all devices that are for both actuation and sensing based on an EAM.

In the invention, combining the actuation signal with the sensing signal can comprise or consist of at least partially superposing the actuation signal with the sensing signal in time. A control system generated this way can provide simultaneous actuation (due to the actuation signal part) and sensing (due to the sensing signal part) capability to the device. This gives a device the capability of sensing during activation. By superposing a lower-amplitude, high frequency sensing signal on top of a higher amplitude primary actuation signal, sensing and actuation functions may be achieved simultaneously, The amplitude of the sensing signal may be significantly less than that of the actuation signal, for example <10%, <5% or even <1% of that of the actuation signal. In this way the deformation response in the actuator may be negligible for the sensing signal compared to that stimulated by the actuation signal. Hence precision, accuracy and stability of the device as an actuator is not compromised.

The first control signal can have a frequency that is less than the sensing signal frequency. For example, the signal level of the first control signal can be substantially constant (DC signal) within a time period for which the sensing signal alternates. Alternatively, the actuation frequency can be a factor of 2, or 5 or 10 or 20 or 50 or 100 or higher than 100 lower than the sensing frequency.

In an embodiment the actuator element is arranged at the inlet portion and configured to adapt the shape of the inlet portion designated to be in contact with the female breast.

Since the shape of the inlet portion designated to be in contact with the female breast can be changed by actuating the actuator element in this embodiment, the inlet portions such as preferably comprising the massage cushion, can be fit to the user's need before expressing. Advantageously, with an improved fit, the suction performance of the breast pump apparatus can be improved and irritation to the user can be avoided. Preferentially, the bending direction of the actuator element can be in a radial or angular direction with respect to a central funnel like tunnel through the inlet portion, or a combination of both. Preferably, the actuator element is arranged at the rear of the contacting element of the inlet portion, such as the massage cushion, such that the massage cushion is in between the actuator element and the female breast during use.

In an embodiment the actuator element is configured to deform based on the sensed pressure. In this embodiment, the actuator element is preferably in close proximity to the skin of the female breast, such as arranged at the inlet portion. Advantageously, the sensed pressure can provide a feedback which can be used for adjusting the deformation of the actuator element until optimum vacuum can be achieved. Expressed differently, the sensed pressure can be used for providing an optimization of the adaptation of the inlet portion to the breast.

In an embodiment the actuator element is configured to detect a lump and to modify the deformation in response to the detection of the lump to reduce pain.

For instance, a lump can be detected from a measured pressure peak in this embodiment. In response to the detected lump, the sensed pressure feedback can, for instance, ensure that the pressure be decreased in order to avoid pain to the user. Alternatively or additionally, a massage function executed through varying actuation of the actuator element can be focused on the lump region in order to aim at relieving the lump.

In an embodiment a plurality of actuator elements is distributed over the inlet portion, in particular radially distributed over the inlet portion.

Also in this embodiment, the inlet portion preferentially comprises a funnel shaped channel and a plurality of actuator elements being distributed over the inlet portion surface, which is to be in contact with the female breast. Preferentially, five actuator elements are radially distributed at equal distances over the inlet portion, wherein in other embodiments also more or less than five actuator elements and/or a non-equal distribution are contemplated. With the example of five actuator elements, an advantageous adjusting of the inlet portion at five different positions can be performed to ensure an optimal fit.

In an embodiment the actuator element is configured to be applied a first control signal and an overlaid second control signal, wherein the first control signal is configured to statically adjust the shape of the actuator element and the second control signal is a faster time varying signal implementing a massage function.

In an embodiment, the massage function includes at least one of increased force and vibration. Preferentially, the difference between increased force and vibration is the frequency and/or the amplitude of the faster time varying signal, which is overlaid onto the first control signal.

Massaging and stimulation of the breast area located around but not including the nipple has a proven positive influence on the milk volume expressed by lactating women. Accordingly, the breast pump apparatus according to this invention allows for an improved milk expression efficiency.

In an embodiment the actuator elements are configured to be controlled individually. The individual control of the actuator elements allows for a further improved individualized adaptation of the shape of the inlet portion to the female breast. In an embodiment the actuator elements can be adjusted manually. Preferentially, the actuation is partly or completely controlled using feedback based on sensed pressure. Thereby, optimum vacuum can be achieved and maintained continuously while operating the breast pump apparatus. Since the actuator elements are spatially arranged preferentially over the inlet portion, a massage pattern, which previously had to be executed manually, becomes possible to be executed through an actuation sequence of the actuator elements. Preferentially, the massage function is implemented by superimposing a further control signal on statically actuated EAPs.

In an embodiment the plurality of actuator elements are spatially arranged to allow the execution of a massage pattern, in particular a spiral massage pattern, in response to the control signal.

Accordingly, statical actuation preferably adjusts the actuator elements to a particular operation position, wherein the massage pattern employs an increased actuation resulting in extra force in a certain area or a vibration signal inducing stimulation of the expression. Preferably, the time series of actuation of the plurality of actuator elements is designed to simulate well-known massage patterns of massaging the breast, such as, for instance, moving the fingers around the breast in a circular motion; moving the fingers in a circular and spiral motion around the breast; and comb the breast with the four fingers besides thumb. However, alternatively or additionally, also other massage patterns are contemplated.

In an embodiment, for the implementation of more complex massage patterns, the plurality of actuator elements comprises actuator arrays, which allow a higher spatial resolution of the actuator elements and therefore a more precise operation of the shape and/or force variation.

In an embodiment the actuator element is arranged at the pump body distant from the portion designated to be in contact with the female breast, wherein a deformation of the actuator element modifies the volume of the pump volume defined inside the pump body.

Preferentially, the actuator element position is substantially opposite to the opening of the inlet portion, in order to avoid for the channel through the inlet portion to become blocked upon deformation of the actuator element. Since the total inner volume of the pump volume is modified through deformation of the actuator element, the free volume within the pump body can be maintained constant, independently from the size of the user's nipple. Since suction performance is affected by the free volume, which affects the build-up of vacuum, and since the free volume can be kept constant, the breast pump apparatus according to this embodiment allows for an improved suction performance independent of the user.

Preferentially, the actuator element is configured to change the pump volume of the pump body approximately 10 ml. This amount is sufficient to account for the difference between small and large nipples.

Preferentially, the embodiment of the actuator element being arranged distant from the portion designated to be in contact with the female breast can be combined with the actuator element provided at the inlet portion as described above.

Preferably, the actuator element comprises a mechanical structure which interacts with the active material upon driving of the active material such that the mechanical structure switches from a first stable state to a second stable state.

A stable mechanical state means a mechanical state that can be, or is maintained without applying an external stimulus such as in particular the driving to the actuator element. Thus, the mechanical arrangement is for maintaining at least the second stable mechanical state upon ceasing of the driving. The first stable mechanical state can be the non-driven equilibrium or rest state of the actuation structure.

This actuator element combines an actuation structure comprising the active material with a mechanical structure so that the device can be actuated and have multiple stable states. The actuation structure interacts with the mechanical structure to activate the device to switch from one to the other state. This means the actuator element only requires a driving when being switched and not when in a stable state.

The actuator element can be used to give a digital output (below a threshold there is no effect and above the threshold there is an effect of constant magnitude) or indeed a multiple level output. Hence, the actuation of an essentially analogue actuation structure is transformed into a digital output. In this way, an analogue drive signal is converted into a digital actuation output, and the actuated state remains after removal of the applied drive signal.

Preferentially, in the application of the breast pump apparatus, the pump body volume can thus be adapted to digitally switch from a larger pump volume to a smaller pump volume, possibly with additional intermediate levels, through activation of the actuator element while no control signal is necessary to maintain the pump body volume in the adjusted state.

Further preferentially, the pressure within the pump volume is sensed by the actuator element and the switching between two of the stable states is controlled by the control signal in case the pressure exceeds a predetermined threshold. For instance, the pressure exceeding a threshold can be indicative of a free pump volume exceeding a preferred range such that the pump volume can be reduced by switching between two stable states of the actuator element. Thereby, an adaptation to a size of the nipple can be achieved without having to continuously provide the control signal to the active element. Further specific examples of bi- and multi-stable actuator devices comprising active materials are disclosed in non-pre-published European patent application number EP15189808.7, to which it is referred.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The breast pump apparatus 100 illustrated in FIG. 1 and in particular pump body 130 thereof has a shape and size which is not controllable.

A breast pump apparatus 1 according to embodiments of the invention, more precisely pump body 130 thereof, further comprises an actuator element 200, 300, 400, which will be discussed with reference to FIGS. 4 to 7 below, which is capable of deforming upon application of a control signal to it. The deformation of the actuator element modifies at least one of a shape and size of the pump volume of pump body 130 and allows an adaptation to the specific user's needs.

In the following, the actuator element 200, 300, 400 comprises an electroactive material (EAM), in particular an electroactive polymer (EAP). Electroactive materials (EAM) are a class of materials within the field of electrically responsive materials. When implemented in an actuation device, subjecting an EAM to an electrical drive signal can make them change in size and/or shape. This effect can be used for actuation and sensing purposes. There exist inorganic and organic EAMs. A special kind of organic EAMs are electroactive polymers (EAPs). Electroactive polymers (EAP) are an emerging class of electrically responsive materials. EAPs, like EAMs can work as sensors or actuators, but can be more easily manufactured into various shapes allowing easy integration into a large variety of systems. Other advantages of EAPs include low power, small form factor, flexibility, noiseless operation, and accuracy, the possibility of high resolution, fast response times, and cyclic actuation. An EAP device can be used in any application in which a small amount of movement of a component or feature is desired, based on electric actuation. Similarly, the technology can be used for sensing small movements. The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-20 kHz.

Figure 2:
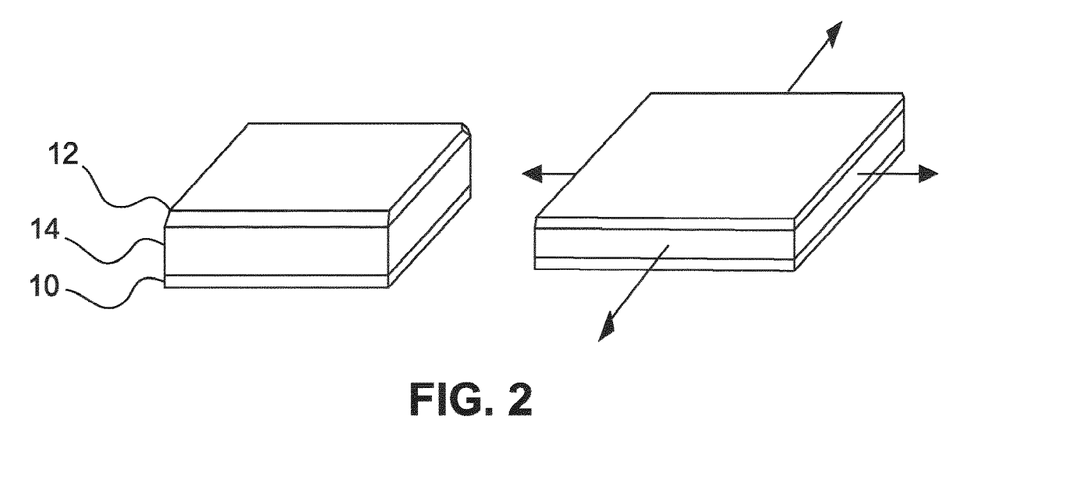
FIG. 2 shows schematically and exemplarily an electroactive polymer device which is not clamped.
Figure 3:
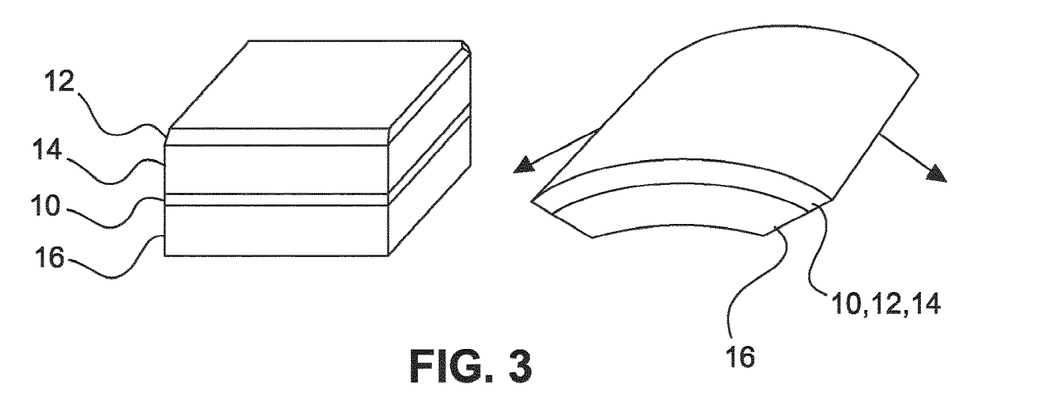
FIG. 3 shows schematically and exemplarily an electroactive polymer device which is constrained by a backing layer.

FIGS. 2 and 3 show two possible operating modes for an electroactive polymer (EAP) device that comprises an EAP layer 14 sandwiched between electrodes 10, 12 on opposite sides of the EAP layer 14. While in FIG. 2 the EAP layer is freely moveable, in FIG. 3 the whole EAP layer and its electrodes are clamped with one side to a support carrier layer 16. A voltage difference (drive signal) applied over the electrodes 10 and 12 is used to provide an electric field over the EAP layer to cause the EAP layer to expand in all directions as shown. While in FIG. 2 this leads to deformation of the EAP layer due to the layer being freely suspended, the same actuation in FIG. 3 leads to bending of the device due to the restrained freedom of motion by the clamping. Using device engineering a vast variety of device outputs can be invoked upon actuation of the EAP layer, i.e. upon driving of the device. Thus, to obtain the asymmetric curving around an axis as shown, molecular orientation (film stretching) may for example be applied, forcing the movement in one direction. The expansion in one direction may result from the asymmetry in the EAP layer, or it may result from asymmetry in the properties of the carrier layer, or a combination of both.

An electroactive polymer (EAP) based device, like those of FIG. 2 and FIG. 3, typically is an analogue device, which means that the drive vs. output response curve is a continuous curve. Hence, any signal other than a zero level/intensity signal will lead to an actuation output. In one example, these devices require continuous driving in order to maintain their actuated state. In other examples, also different examples of EAP based devices are contemplated, for instance which maintain in their actuated state. Alternatively or additionally, also other actuator elements different from EAP based devices are contemplated, such as optoactive polymer (OAP) based devices and the like.

Further, for certain classes of EAP, application of a small force (mechanical load) to the device generates an electrical signal in response. This allows a single EAP structure to be used both for actuation and for sensing.

Figure 4:
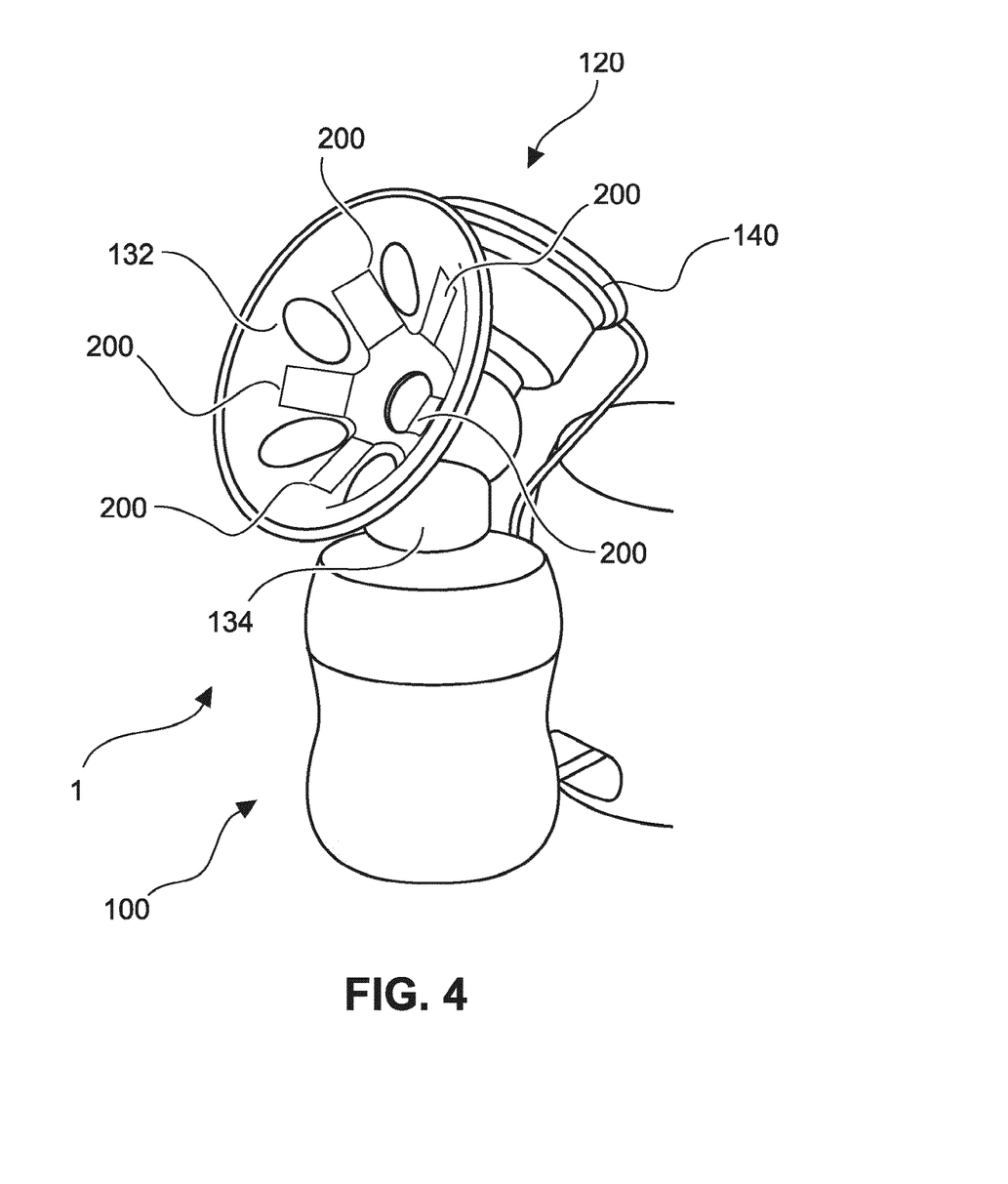
FIG. 4 shows schematically and exemplarily a first example of a breast pump apparatus according to the invention.

FIG. 4 shows schematically and exemplarily a first example of a breast pump apparatus 1 according to the invention. A plurality of components of breast pump apparatus 1 are identical to those of breast pump apparatus 100 described with reference to FIG. 1 above and the description thereof is thus omitted.

In addition, breast pump apparatus 1 comprises five actuator elements 200 disposed radially around a central opening of inlet portion 132. A bending direction of the actuator elements 200 can be in radial or angular direction or a combination of both. When actuated, the shape of inlet portion 132 changes. In one example, inlet portion 132 is formed as a massage cushion, wherein control of the actuator elements 200 results in an adapted shape of the massage cushion. In this example, actuator elements 200 are individually controlled so that the shape of inlet portion 132 can be fitted according to the preferences of the user prior to expression. As indicated above, a good fit can improve the suction performance of breast pump apparatus 1 and can avoid pain or irritation for the user.

Deformation of the actuator elements 200 is controlled by providing a control signal to each of actuator elements 200. The shape adaptation induced by actuator elements 200 can be adjusted manually, such as by pressing a button on a control unit of breast pump apparatus 1, or automatically via feedback from a pressure sensor, which can control the adjustment of each actuator element 200 until an optimum vacuum is achieved. The actuator element 200 itself can be operated as a pressure sensor using, for instance, a different control signal as described above. While five actuator elements 200 have been employed in this example, the amount of actuator elements 200 can be varied as needed.

In addition to implementing an adaptation of shape of inlet portion 132, breast pump apparatus 1 can further implement a massage function through, for instance, superimposing a second control signal on actuator elements 200, which are usually statically controlled in order to maintain a desired deformed shape. Depending on the superimposed control signal, an increased force in a certain area, which requires individual control of each actuator element 200, or a vibration signal, which induces stimulation of the expression, can be performed. In one example, the actuator elements 200 are actuated in sequence to simulate massage patterns on the breast.

Figure 5:
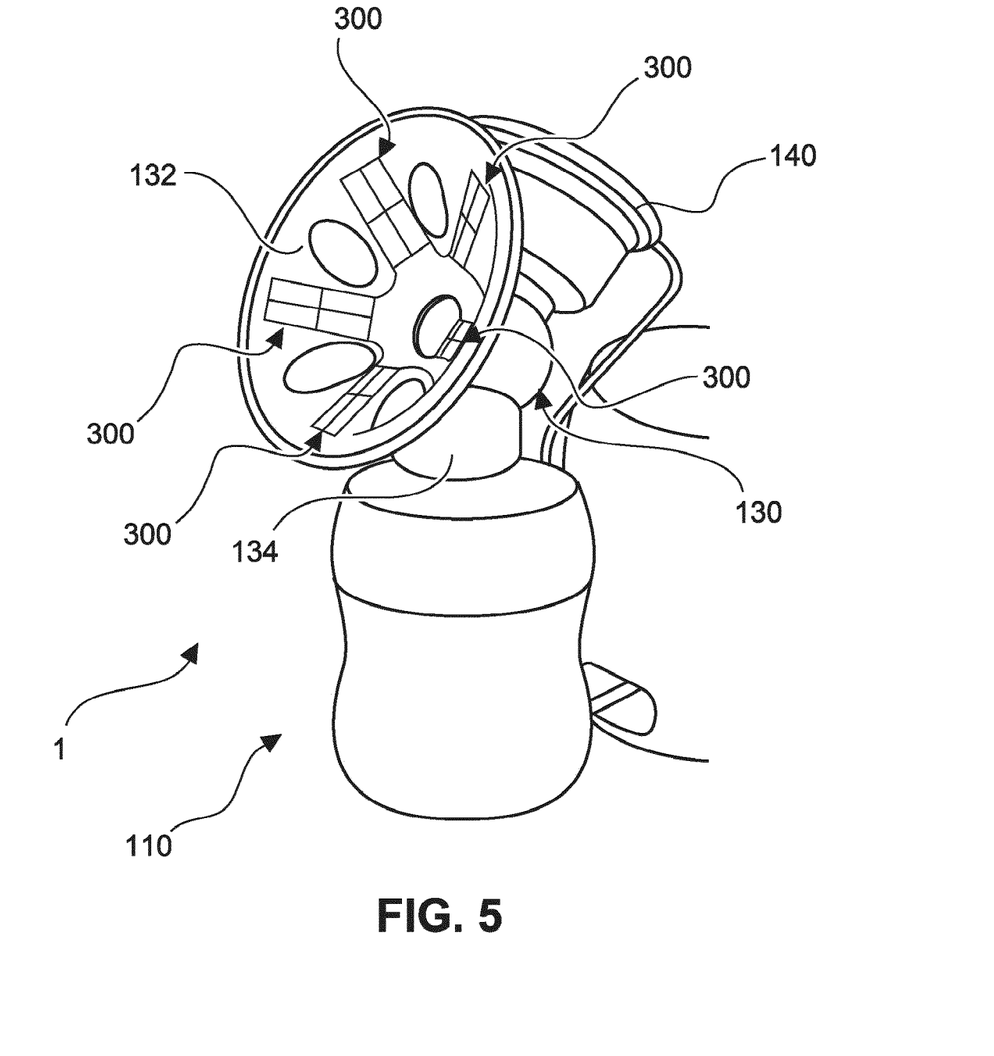
FIG. 5 shows schematically and exemplarily a second example of a breast pump apparatus according to the invention.

FIG. 5 shows a further example of breast pump apparatus 1 schematically and exemplarily, which implements actuator element arrays 300 instead of actuator elements 200 shown in FIG. 4. In this example, each actuator element array 300 is divided into four individually controllable actuator element sections, resulting in an increased spatial resolution of deformations that can be carried out by controlling actuator element arrays 300. For example, more complex massage patterns for massaging the breast as will be described with reference to FIG. 6 can be implemented through operation of actuator element arrays 300.

Figure 6A:
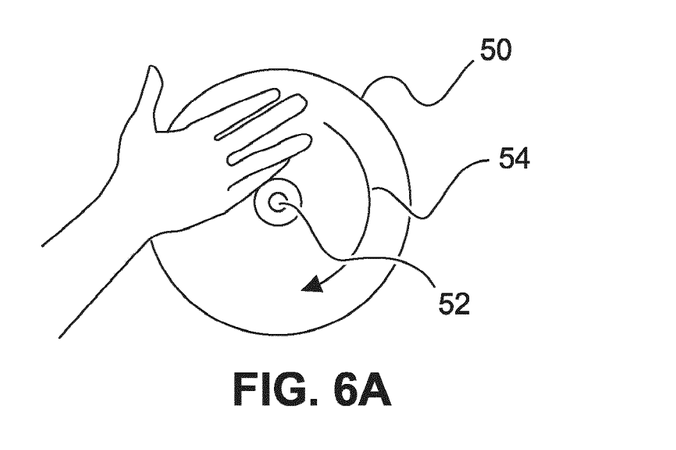
FIG. 6A-6C show schematically and exemplarily examples of massage patterns implemented in the breast pump apparatus according to FIG. 5, FIGS. 7A and 7B show schematically and exemplarily a third example of a breast pump apparatus according to the invention.
Figure 6B:
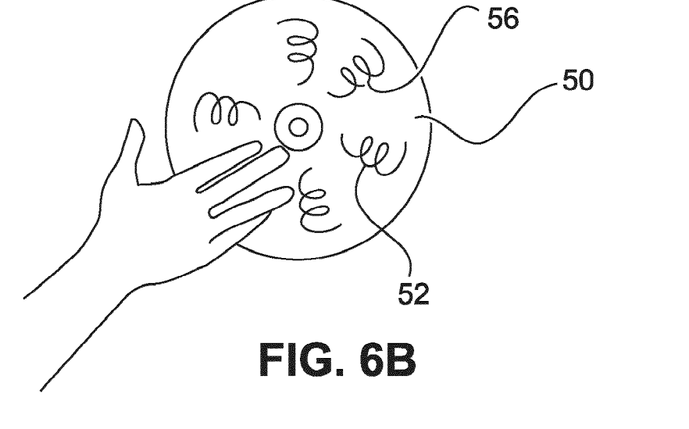
Figure 6C:
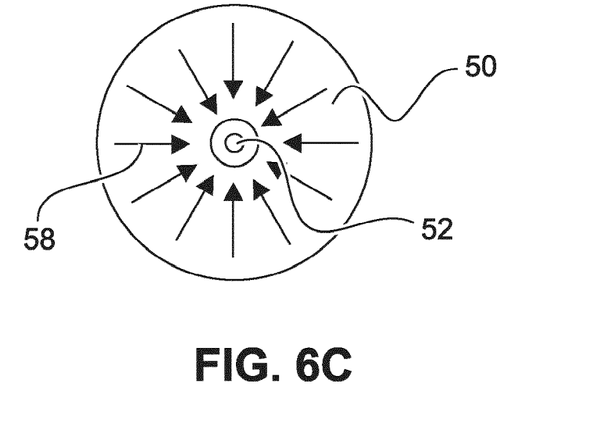

FIGS. 6A to 6C show three non-limiting examples of suitable patterns for massaging the breast and in particular the breast excluding the nipple. These examples have shown to be efficient in order to increase the milk expression when done manually in the past. In accordance therewith, these patterns have shown to be beneficial when implemented in an automatic manner in breast pump apparatus 1. Each of FIGS. 6A to 6C shows schematically and exemplarily a breast 50 with a nipple 52 located in the center of breast 50.

In FIG. 6A, an arrow 54 indicates a circular motion on the breast area around but not including the nipple 52. This circular motion can be repeated as desired.

In FIG. 6B, a circular and spiral motion 56 starting from the edge and continuing around the breast is illustrated. It is started at the edge of the breast and moved towards the nipple 52. If a lump is encountered, more time is applied on it in order to make it more likely that the woman feels no pain.

In FIG. 6C a comb shaped pattern 58 is illustrated, in which pressure starts from the edge of the breast and advances as several fingers or teeth of the comb towards the nipple 52.

Preferably, the massage patterns of FIG. 6A, FIG. 6B and FIG. 6C are implemented by breast pump apparatus 1 in this sequence. However, also other sequences of these massage patterns or alternative/additional massage patterns can of course be used.

Figure 7A:
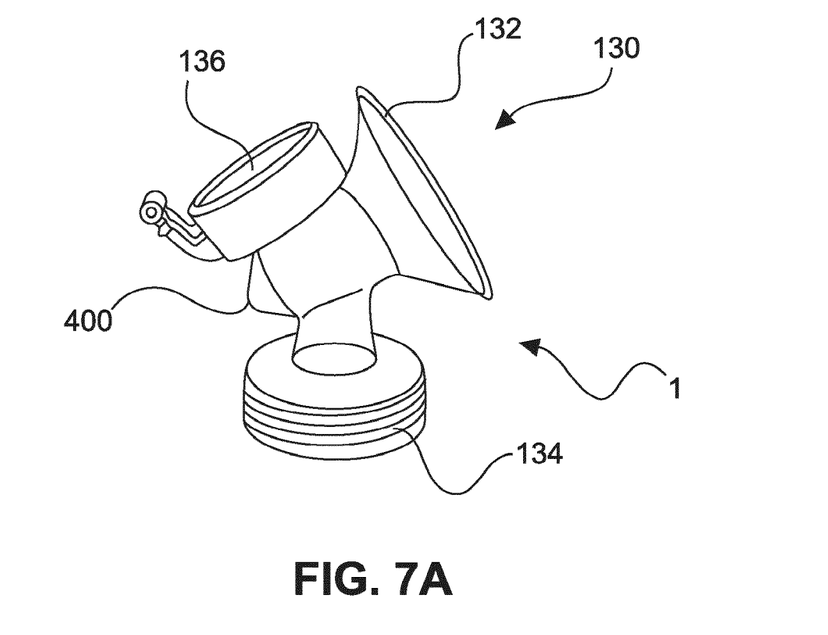
Figure 7B:
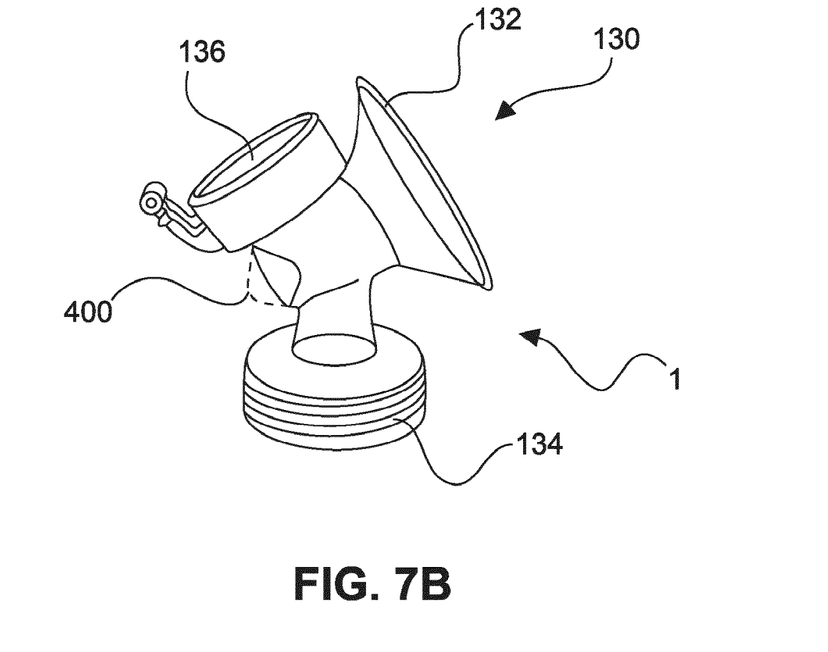

FIGS. 7A and 7B show schematically and exemplarily two views on a third example of a breast pump apparatus 1, more precisely of pump body 130 thereof including a third embodiment of actuator element 400.

In FIGS. 7A and 7B, in addition to inlet portion 132 and outlet portion 134, a pumping device mounting portion 136 is illustrated. A manual or electronic pumping device, such as pumping device 140 illustrated in FIGS. 4 and 5, can be mounted on pumping device mounting portion 136. A negative pressure can then be applied and maintained within a pump volume defined within pump body 130 through operation of pumping device 140.

Actuator element 400 is shown at a position opposite to inlet portion 132, i.e. at a position distant from the user's nipple when having the breast pump apparatus 1 in operation and the breast seamlessly fitted against inlet portion 132. In FIG. 7A, actuator element 400 is shown deflected outwardly, while it is bent inwardly in FIG. 7B. By bending to the inside, actuator element 400 reduces the pump volume within pump body 130. Thereby, by actuation of actuator element 400, the free volume within pump body 130 is maintained substantially constant despite varying sizes of nipples, such that a suction efficiency can be ensured. Preferably, the volumetric displacement is in the order of magnitude of 10 ml, wherein also other magnitudes are of course contemplated.

Preferably, actuator element 400 can in the way described above act simultaneously as a pressure sensor and actuator, wherein a feedback loop can then be employed to compensate for pressure variation. Pressure variation causes a force on the actuator element 400, which can then be used for deflecting, if needed. Additionally or alternatively, actuator element 400 can have a bi-stable or multi-stable configuration to avoid the effects of pressure variation, wherein the actuator element 400 then can remain in the deflected position without the continuing need for application of the control signal.

Figures 8A, 8B:
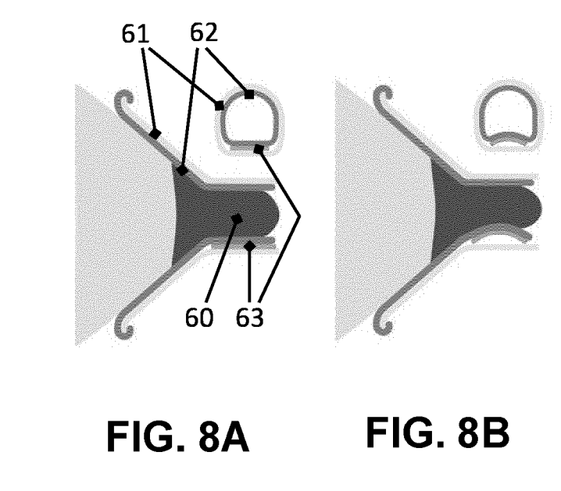
FIGS. 8A, 8B, 8C and 8D show schematically and exemplarily an embodiment of a breast pump in accordance with the invention with a single EAP in the funnel.
Figure 8C:
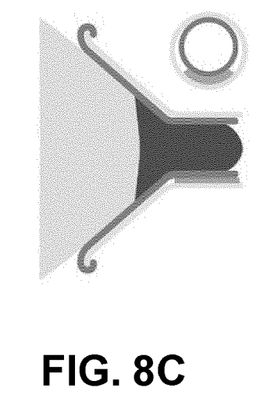
Figure 8D:
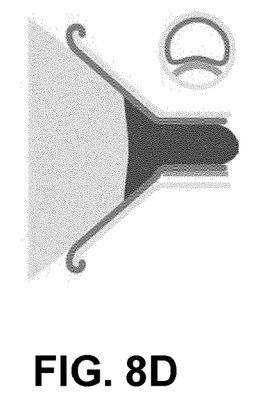

FIGS. 8A, 8B, 8C and 8D show an embodiment of a single EAP in the funnel to mimic baby tongue pressure. In this exemplary embodiment one EAP insert (63) is used and positioned in between the hard plastic funnel (61) and the cushion (62). When a voltage is applied on the EAP (63), it will stretch and, due to the carrier layer, the composite will bend as shown in FIGS. 8B and 8D. This can either by a flat composite (FIGS. 8A and 8B) or a curved shaped composite (FIGS. 8C and 8D). These EAPs can also be used to measure forces that the nipple (60) exerts on that position on the wall.

Figure 9A:
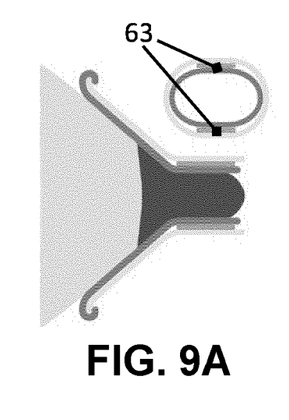
FIGS. 9A and 9B show schematically and exemplarily an embodiment of a breast pump in accordance with the invention with multiple EAPs in the funnel.
Figure 9B:
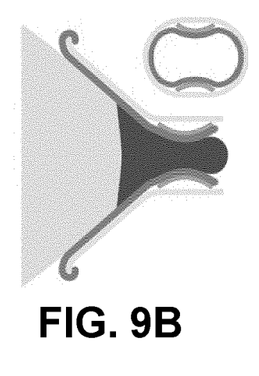
Figure 10A:
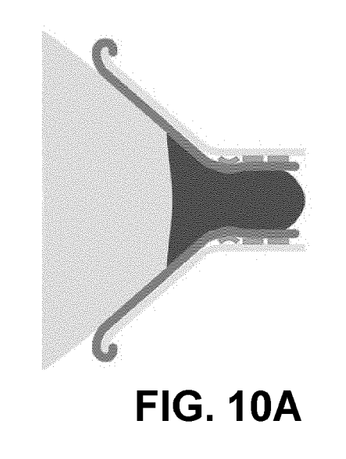
FIGS. 10A, 10B and 10C show schematically and exemplarily another embodiment of a breast pump in accordance with the invention with multiple EAPs in the funnel.
Figure 10B:
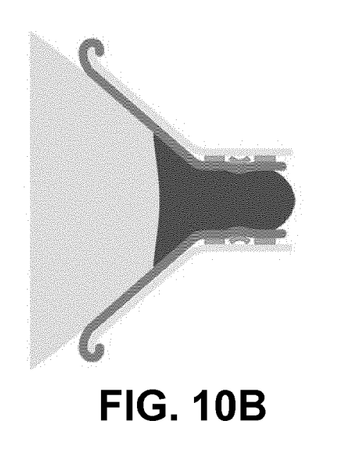
Figure 10C:
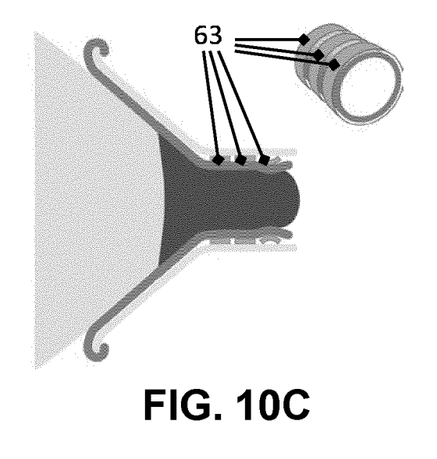

FIGS. 9A, 9B, 10A, 10B and 10C show the use of two or more EAPs to mimic baby behavior, or to measure the forces at multiple spots. In this embodiment multiple EAPs are used to mimic the baby lips' motion. For example, 2 EAPs (63) facing each other are used to mimic the baby lips as shown in FIGS. 9A and 9B. Instead of two EAPs, an EAP in the form of a ring can also be placed around the nipple to exert a uniform pressure onto the nipple. Multiple EAPs (63), e.g. in the form of 3 successive rings, can also be used to make a peristaltic rolling motion as shown in FIGS. 10A, 10B and 10C.

Figure 11A:
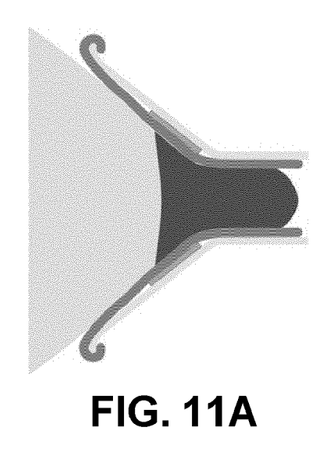
FIGS. 11A and 11B show schematically and exemplarily still another embodiment of a breast pump in accordance with the invention with multiple EAPs in the funnel.
Figure 11B:
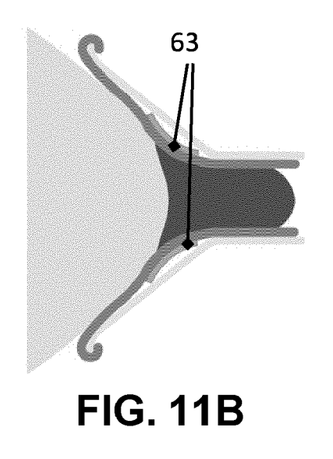
Figure 12A:
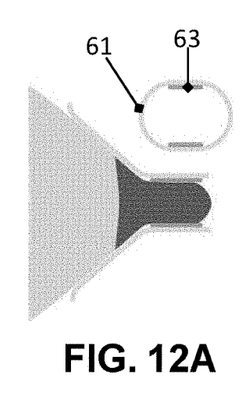
FIGS. 12A, 12B, 12C and 12D show schematically and exemplarily another embodiment of a breast pump in accordance with the invention.
Figure 12B:
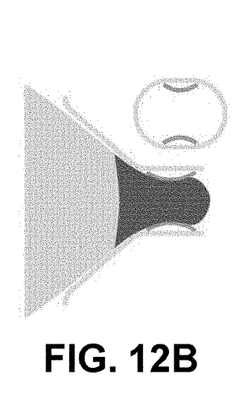
Figure 12C:
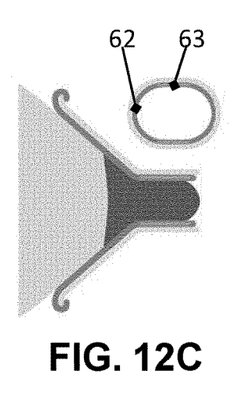
Figure 12D:
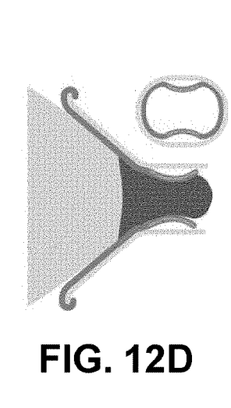

FIGS. 11A and 11B show an embodiment where EAPs (63) are positioned such that they stimulate the areola tissue in order to get a faster Milk Ejection Reflex MER or a more comfortable experience.

In all above embodiments, the EAPs are positioned between the hard plastic funnel and the soft cushion. However, the EAPs (63) can also be directly positioned onto or embedded in the hard plastic funnel (61) or in the cushion (62) as shown in FIGS. 12A and 12B, or FIGS. 12C and 12D, respectively.

Figure 13:
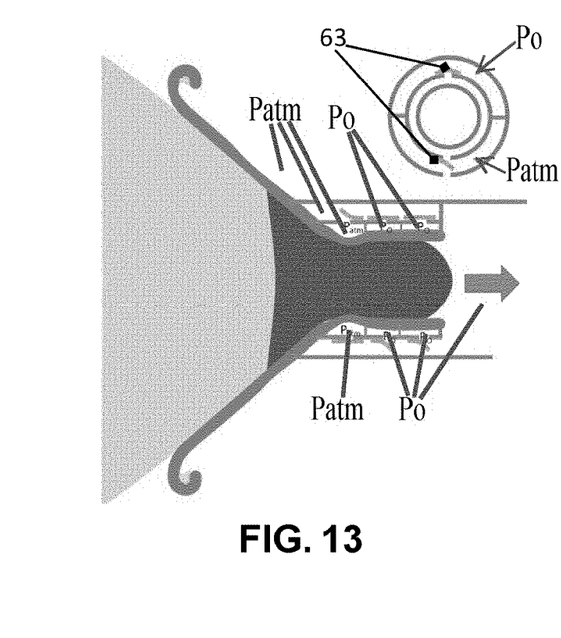
FIG. 13 shows schematically and exemplarily another embodiment of a breast pump in accordance with the invention.

FIG. 13 shows an embodiment where EAP valves (63) regulate pressure between two pressure levels Po and Patm to realize alternating pressure on the lactiferous ducts. In this another alternative embodiment, the EAP acts as a valve which regulates the air pressure in a cavity surrounding the nipple. The cavity is connected to the vacuum of the pump (Po) and also to ambient (Patm), with the EAP acting as a switch to control between both pressure states and create a peristaltic pressure motion. The EAP in off state blocks the air vent to ambient and an actuated EAP blocks the under pressure (Po), so that the cavity can be regulated between the two states. The cavities as such are designed to compress the nipple slightly at ambient pressure. Be actuating the EAP, the under pressure is removed locally and the (air-filled) cavity exerts a pressure on the nipple. If multiple EAP valves are present and are operated in a sequence this could mimic the baby suckling behavior. This embodiment could potentially create more pressure and stroke than a single EAP could deliver. An embodiment is shown on FIG. 13 by way of an example. The example has two EAP valves per cavity. Embodiments with one valve per cavity are also possible.

Although in the detailed description herein above the construction and operation of the breast pump apparatus according to the invention has been described for EAPs, the invention can in fact be used for devices based on other kinds of EAM material. Hence, unless indicated otherwise, the EAP materials hereinabove can be replaced with other EAM materials. Such other EAM materials are known in the art and the person skilled in the art will know where to find them and how to apply them. A number of options will be described herein below.

A common sub-division of EAM devices is into field-driven and current or charge (ion) driven EAMs. Field-driven EAMs are actuated by an electric field through direct electromechanical coupling, while the actuation mechanism for current or charge driven EAMs involves the diffusion of ions. The latter mechanism is more often found in the corresponding organic EAMs such as EAPs. While Field driven EAMs generally are driven with voltage signals and require corresponding voltage drivers/controllers, current driven EAMs generally are driven with current or charge signals sometimes requiring current drivers. Both classes of materials have multiple family members, each having their own advantages and disadvantages.

Field driven EAMs, can be organic or inorganic materials and if organic can be single molecule, oligomeric or polymeric. The organic materials and especially polymers are an emerging class of materials of growing interest as they combine the actuation properties with material properties such as light weight, cheap manufacture and easy processing.

The field driven EAMs and thus also EAPs are generally piezoelectric and possibly ferroelectric and thus comprise a spontaneous permanent polarization (dipole moment), are electrostrictive and thus comprise only a polarization (dipole moment) when driven, but not when not driven or are dielectric relaxor materials. Such polymers include, but are not limited to, the sub-classes: piezoelectric polymers, ferroelectric polymers, electrostrictive polymers, relaxor ferroelectric polymers, dielectric elastomers, liquid crystal elastomers.

The lack of a spontaneous polarization means that electrostrictors display little or no hysteretic loss even at very high frequencies of operation. The advantages are however gained at the expense of temperature stability. Relaxors operate best in situations where the temperature can be stabilized to within approximately 10° C. This may seem extremely limiting at first glance, but given that electrostrictors excel at high frequencies and very low driving fields, then the applications tend to be in specialized micro actuators. Temperature stabilization of such small devices is relatively simple and often presents only a minor problem in the overall design and development process.

A first notable subclass of Field driven EAPs are piezoelectric and electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of dielectric elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

Another notable subclass of Ionic polymers is Conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In one example the EAM or EAP material is an electrostrictive polymer, such as a relaxor ferroelectric material. Such materials can have an electrostrictive constant that is high enough for good practical use, i.e. advantageous for simultaneous sensing and actuation functions. Relaxor ferroelectric materials are non-ferroelectric when zero driving field (i.e. voltage) is applied to them, but become ferroelectric during driving. Hence there is no electromechanical coupling present in the material at non-driving. The electromechanical coupling becomes non-zero when a drive signal is applied and can be measured through applying the small amplitude high frequency signal on top of the drive signal, in accordance with the procedures described above. Relaxor ferroelectric materials, moreover, benefit from a unique combination of high electromechanical coupling at non-zero drive signal and good actuation characteristics.

The most commonly used examples of inorganic relaxor ferroelectric materials are: lead magnesium niobate (PMN), lead magnesium niobate-lead titanate (PMN-PT) and lead lanthanum zirconate titanate (PLZT). But other are known in the art.

Examples of field-driven EAPs are piezoelectric polymers, ferroelectric polymers, electrostrictive polymers (such as PVDF based relaxor polymers or polyurethanes), dielectric elastomers and liquid crystal elastomers (LCE). Thus, preferably the EAP material is a relaxor ferroelectric polymer such as e.g. PVDF based relaxor ferroelectric based polymer. Such materials can be any one chosen from the group of materials herein below.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The current driven EAMs and EAPs comprise conjugated polymers, Ionic Polymer Metal Composites, ionic gels and polymer gels.

Examples of ionic-driven EAPs are conjugated polymers, carbon nanotube (CNT) polymer composites and ionic polymer-metal composites (IPMC). An ionic polymer-metal composite (IPMC) is a synthetic composite nanomaterial that displays artificial muscle behavior under an applied voltage or electric field.

The sub-class dielectric elastomers includes, but is not limited to: acrylates, polyurethanes, silicones.

The sub-class conjugated polymers includes, but is not limited to: polypyrrole, poly-3,4-ethylenedioxythiophene, poly(p-phenylene sulfide), polyanilines.

The materials above can be implanted as pure materials or as materials suspended in matrix materials. Matrix materials can comprise polymers.

To any actuation structure comprising EAM material, additional passive layers may be provided for influencing the behavior of the EAM layer in response to an applied drive signal.

In some cases, thin film electrodes are added when the polymer itself lacks sufficient conductivity (dimensionwise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The invention claimed is:

1. A breast pump apparatus for expressing breast milk, comprising:
   a container unit for receiving expressed breast milk; and
   a pump unit including a pump body and a pumping device for applying negative pressure to a pump volume defined by the pump body,
   wherein the pump body comprises an inlet portion adapted to be received on a female breast, an outlet portion adapted to channel expressed milk to the container unit, and an actuator element comprising an active material capable of deforming upon application of at least one control signal and configured to have a bi-stable or multi-stable configuration,
   wherein a deformation of the actuator element in response to the at least one control signal modifies at least one of a shape or a size of the pump volume defined by the pump body to maintain a substantially constant free volume within the pump body when the inlet portion is in contact with the female breast, and wherein the actuator element is arranged at the pump body distant from the inlet portion.

2. The breast pump apparatus according to claim 1, wherein the actuator element comprises an electroactive polymer.

3. The breast pump apparatus according to claim 2, wherein the electroactive polymer comprises an ionic electroactive polymer.

4. The breast pump apparatus according to claim 1, wherein the actuator element is further configured to operate as a pressure sensor.

5. The breast pump apparatus according to claim 4, wherein the actuator element is configured to deform based on a sensed pressure.

6. The breast pump apparatus according to claim 5, wherein a feedback loop is employed to compensate for pressure variation based on the sensed pressure.

7. The breast pump apparatus according to claim 1, further comprising a plurality of additional actuator elements distributed over the inlet portion.

8. The breast pump apparatus according to claim 7, wherein a deformation of each additional actuator element of the plurality of additional actuator elements in response to the at least one control signal modifies a shape of the inlet portion.

9. The breast pump apparatus according to claim 8, wherein each additional actuator element of the plurality of additional actuator elements is arranged at the inlet portion.

10. The breast pump apparatus according to claim 9, wherein the plurality of additional actuator elements are configured to detect a lump in the female breast, and the deformation of at least one additional actuator element of the plurality of additional actuator elements is modified in response to the detection of the lump to reduce pain.

11. The breast pump apparatus according to claim 9, wherein the at least one control signal comprises a first control signal and an overlaid second control signal, wherein application of the first control signal to each additional actuator element statically adjusts a shape of the additional actuator element, and wherein application of the second control signal to each additional actuator element implements a massage function, wherein the massage function includes at least one of increased force or vibration.

12. The breast pump apparatus according to claim 11, wherein the second control signal is a faster time varying signal than the first control signal.

13. The breast pump apparatus according to claim 8, wherein the plurality of additional actuator elements are spatially arranged to allow execution of a massage pattern in response to the at least one control signal.

14. A breast pump apparatus for expressing breast milk, comprising:
   a pump body defining a pump volume; and
   a pumping device configured to apply negative pressure to the pump volume,
   wherein the pump body comprises an inlet portion adapted to be in contact with female breast, an outlet portion adapted to channel expressed milk from the female breast to a container unit, and a plurality of actuator elements distributed over the inlet portion, each actuator element comprising an active material capable of deforming upon application of at least one control signal,
   wherein a deformation of each actuator element of the plurality of actuator elements in response to the at least one control signal modifies a shape of the inlet portion, and wherein the plurality of actuator elements are spatially arranged to allow execution of a massage pattern in response to the at least one control signal, and
   wherein at least one actuator element of the plurality of actuator elements is configured to operate as a pressure sensor.

15. The breast pump apparatus according to claim 14, wherein the plurality of additional actuator elements are configured to be controlled individually in response to the at least one control signal.

16. The breast pump apparatus according to claim 14, wherein the plurality of actuator elements are distributed radially over the inlet portion.

17. The breast pump apparatus according to claim 14, wherein the massage pattern comprises a spiral massage pattern.

18. The breast pump apparatus according to claim 14, wherein the at least one control signal comprises a first control signal and an overlaid second control signal, wherein application of the first control signal modifies the shape of the inlet portion, and application of the second control signal implements execution of the massage pattern.

19. A breast pump apparatus for expressing breast milk, comprising:

a pump body defining a pump volume; and a pumping device configured to apply negative pressure to the pump volume, wherein the pump body comprises an inlet portion adapted to be in contact with a female breast, an outlet portion adapted to channel expressed milk from the female breast to a container unit, and a plurality of actuator elements distributed over the inlet portion, each actuator element comprising an active material capable of deforming upon application of at least one control signal, wherein a deformation of each actuator element of the plurality of actuator elements in response to the at least one control signal modifies a shape of the inlet portion, and wherein the plurality of actuator elements are spatially arranged to allow execution of a spiral massage pattern in response to the at least one control signal, and wherein the plurality of actuator elements are configured to detect a lump, and the deformation of at least one actuator element of the plurality of actuator elements is modified in response to the detection of the lump.

20. The breast pump apparatus according to claim 19, wherein at least one actuator element of the plurality of actuator elements is further configured to operate as a pressure sensor.

* * * * *